United States Patent [19]

Davis

[11] Patent Number: 5,143,717
[45] Date of Patent: Sep. 1, 1992

[54] BURN FOAM AND DELIVERY SYSTEM
[75] Inventor: Richard C. Davis, Tampa, Fla.
[73] Assignee: Code Blue Medical Corporation, Clearwater, Fla.
[21] Appl. No.: 388,735
[22] Filed: Aug. 2, 1989

Related U.S. Application Data

[63] Continuation of Ser. No. 139,542, Dec. 30, 1987, abandoned.
[51] Int. Cl.⁵ .................. A61K 9/12; A61K 31/635; A61K 33/38; A61K 35/74
[52] U.S. Cl. .................. 424/45; 424/618; 424/641; 424/405; 424/DIG. 13; 514/941; 514/945
[58] Field of Search .............. 424/45, 78, 45; 514/157, 495, 938

[56] References Cited
U.S. PATENT DOCUMENTS

| | | | |
|---|---|---|---|
| 2,338,416 | 1/1944 | Fales | 424/78 |
| 3,761,590 | 9/1973 | Fox, Jr. | 424/78 |
| 3,792,161 | 2/1974 | Fox, Jr. | 424/78 |
| 3,970,584 | 7/1976 | Hart et al. | 424/45 |
| 4,005,191 | 1/1977 | Clark | 424/78 |
| 4,046,886 | 9/1977 | Smith | 424/45 |
| 4,154,823 | 5/1979 | Schutt | 424/78 |
| 4,241,048 | 12/1980 | Durbak et al. | 424/45 |
| 4,495,168 | 1/1985 | Schmolka | 424/78 |
| 4,534,958 | 8/1985 | Adams | 424/45 |
| 4,534,959 | 8/1985 | Schmolka | 424/78 |
| 4,752,465 | 6/1988 | Mackles | 424/45 |
| 4,981,677 | 1/1991 | Thau | 424/45 |

*Primary Examiner*—Thurman K. Page
*Assistant Examiner*—E. J. Webman
*Attorney, Agent, or Firm*—Griffin Branigan & Butler

[57] ABSTRACT

An antibiotic formulation useful in the treatment of burns and abrasions and adapted for topical application as a clinically water soluble foam, the process for preparing the formulation and a special dispenser system for applying same.

12 Claims, 1 Drawing Sheet

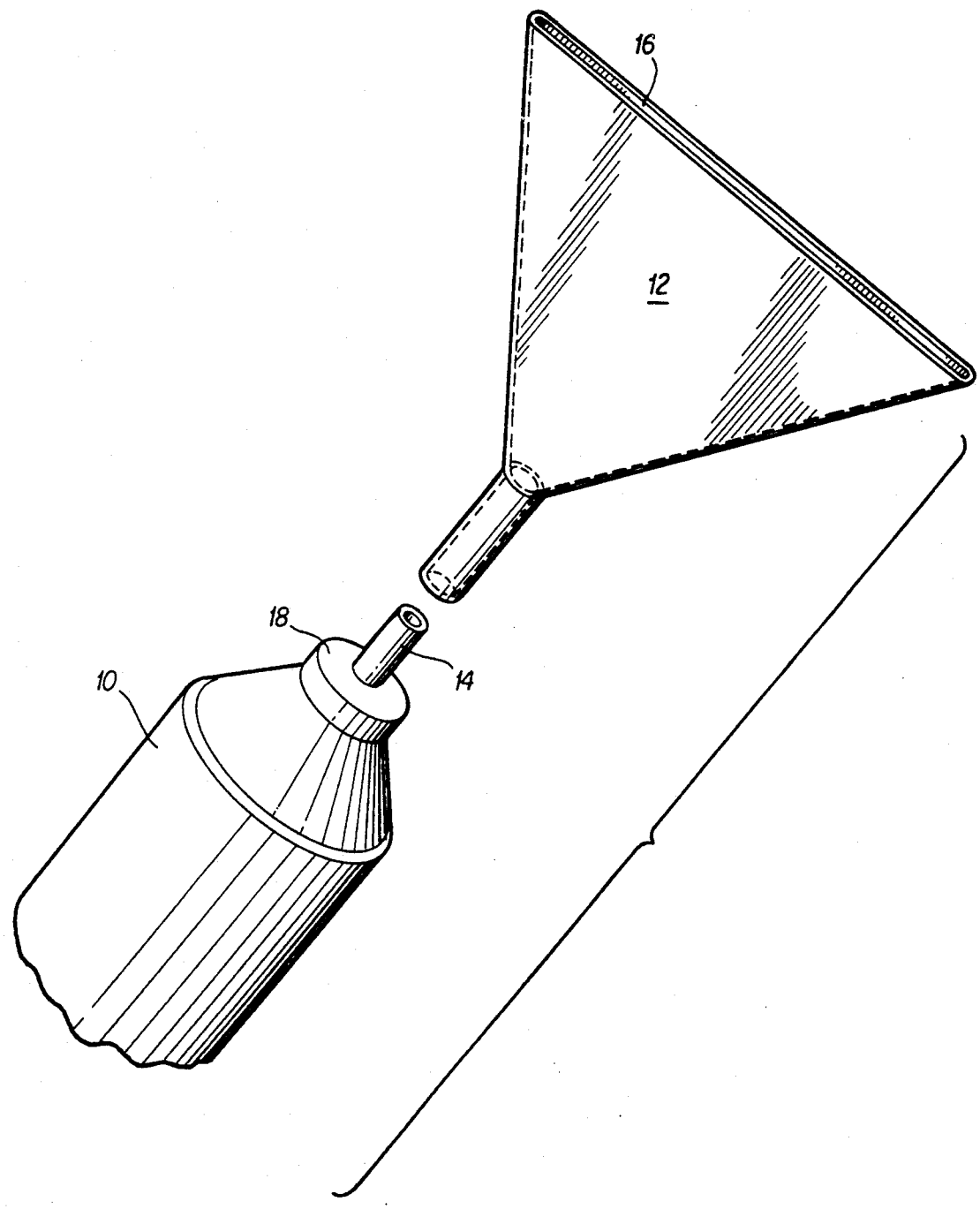

BURN FOAM AND DELIVERY SYSTEM

This is a continuation of application Ser. No. 07/139,542, filed Dec. 30, 1987, now abandoned.

FIELD OF THE INVENTION

This invention relates generally to antibiotic ointments and relates particularly to antibiotic formulations adapted for topical application as a clinically water soluble foam and useful in treatment of burns and abrasions.

BACKGROUND OF THE INVENTION

A burn is probably the most traumatic and severe injury that the human body can sustain and still survive. The major problem is that if the burn itself does not prove fatal, the infection that follows might. A severe thermal burn removes the upper protective layers of the dermis and epidermis as well as disrupting the immunological barriers to infection. It retards regrowth of normal skin and promotes collagen formation which leads to scarring.

The therapeutic use of silver sulfadiazine in successfully treating thermal burns in man and animal is well documented. For example, U.S. Pat. No. 3,761,590 to Fox describes a process for preparing a thick cream ointment containing silver sulfadiazine useful in burn treatment and this disclosure is incorporated herein by reference.

It has been clinically shown that these silver sulfadiazine cream ointments are very effective in the treatment of burn and abrasive injuries to the skin by preventing bacterial infections, especially from Pseudomonas strains. However, in addition to the objectionable odor, cream silver sulfadiazine ointments are very poorly water-soluble, making them extremely difficult and painful to remove from the burn area. This also results in excessive product waste and expense, in addition to the time-consuming task of applying and removal of the ointment. There is thus a definite need in the art for an inexpensive, easy to apply silver sulfadiazine formulation that is painless to the patient when applied, and that is clinically water soluble permitting it to be washed off instantly with minimum discomfort to the patient.

BRIEF DESCRIPTION

Accordingly, it is an object of the present invention to provide a silver sulfadiazine formulation that has all the advantageous features of presently used formulations while minimizing the disadvantages thereof.

It is another object of the present invention to provide a novel antibiotic formulation adapted for topical application as a clinically water soluble foam.

Another object of the present invention is to provide an improved antibiotic formulation that may be easily, quickly and relatively painlessly applied to abrasions or burns and is essentially water soluble to permit easy removal with a minimum of pain to the patient.

It is a further object of the present invention to provide a successful and useful foam antibiotic.

According to the present invention the foregoing and additional objects are attained by providing a specific formulation of an antibiotic suspended in an oil-in-water emulsion that includes specific quantities of white petrolatum, a fatty alcohol, an emollient, an emulsifying agent, a humectant, a preservative and water. This suspension is aerosolized at a specific pressure by a specific inactive aliphatic hydrocarbon.

BRIEF DESCRIPTION OF THE DRAWINGS

The foregoing and other objects, features and advantages of the invention will be apparent from the following more particular description of a preferred embodiment of the invention, as illustrated in the accompanying drawing. The drawing is not necessarily to scale, emphasis being placed upon illustrating principles of the invention in a clear manner.

The drawing is a fragmented, isometric, exploded view of a dispenser can having the foam of this invention therein with a particular dispenser nozzle for use with the foam of this invention.

DETAILED DESCRIPTION

The silver sulfadiazine containing oil-in-water emulsion is prepared essentially as described in U.S. Pat. No. 3,761,590. The silver sulfadiazine is obtained in small granular white powder form and added to a mixture of white petrolatum, a fatty alcohol (stearyl alcohol), an emollient (isopropyl myristate), an emulsifying agent (sorbitan monooleate and polyoxyl 40 stearate) a humectant (propylene glycol), a preservant (methylparaben) and distilled water. These ingredients are agitated by stirring while heating to approximately 75° C. with this temperature and stirring maintained until all ingredients are in the liquid state and the oil-in-water emulsion is obtained. After permitting the mixture to cool slightly, the liquid is placed into pressurized cans 10 at thirty-five pounds per square inch pressure using A-46 as the pressurized propellant. A-46 is formed of 85% isobutane and 15% propane and acts to stabilize each foam bubble.

A foam, such as that formed by the formulation of the present invention, is a complex structure. Each compound which is foamed must be able to sustain certain physical characteristics under the stress of forming a very thin, curved, or bubble surface containing an internal gaseous substance which dynamically interacts with the external gaseous environment and the atmospheric pressures encountered. The film surface is exposed to osmotic pressures, diffusion gradients, pH differences, temperature differences, and humidity differences. These, along with the physical environmental stresses of temperature, air flow, humidity, and others, will give each foam compound many of its characteristics. The chemistry of a foamed compound itself is also critical. Most foams work best when the compound is a suspension of water soluble and water insoluble components, as in the present invention.

The chemical structure of silver sulfadiazine is such that the molecule tends to be linear, rather than globular, with one end being more hydrophyllic or "water-attracting" than the other. This fact makes it a "solubly polar" substance, with one end tending to be water soluble and the other being virtually insoluble in water. The overall effect is that the compound is clinically poorly water soluble.

The specific formulation and method of producing a stable foam with sustained antimicrobial activity and the requisite application and solubility characteristics of the present invention results in a foam with an intricate bubble architecture resembling a micelle. This permits the formation of an extremely water soluble silver sulfadiazine foam formulation having all the bactericidal potency of the prior art insoluble cream ointment of silver sulfadiazine.

A micelle is the fundamental structure of all living things, and is basically, a hollow chamber surrounded by a surface such as a film or membrane. This structure utilizes physiochemical and electrochemical differences between the internal and external environments to create a stable architecture, facilitate transport of substances across the membrane, and many other complex functions. Each living cell in the human body is a micelle. Each is a dynamic little, hollow factory, specializing in some unique task for which it is designed. If you consider a micelle as being like an inflated basketball, the rubber skin of the basketball acts like a cell membrane. The big difference is that basketballs have air both on the inside and the outside of the skin which separates them, and good basketballs do not leak. Micelles, on the other hand, have a porous membrane which is designed for controlled leakage, both into and out of the cell.

The molecules making up the membrane layer of micelles, tend to be linear in their geometry and may be pictured as each resembling a wooden match having one end with a tail, the other with a head. Picture the thickness of the cell membrane as composed of an array of millions of these matches (molecules) all aligned and stuck together perpendicularly with their "heads" at one end on the outer surface facing away from the hollow chamber inside, and their "tails" at the other end pointing down into the hollow chamber. The interiors of most cells are hydrophobic or water-repelling. In this instance the "tails" of the molecules which make up this membrane layer, contain fat-soluble compounds which do not mix well with water. The exterior surface or "heads" of the molecules contain hydrophyllic or water-attracting compounds which dissolve easily in water. The micelle membrane then acts like a barrier separating water-attracting and water-repelling environments and complex chemical reactions which take place in both.

The chemical constituents of the present invention, combined with an appropriate amount of surface water, balanced by an appropriate internal (propellant) gas, mixed properly, at appropriate temperatures and pressures allows for the formation of an architecture referred to as a "foam". Since the present invention mixture contains both hydrophyllic and hydrophobic components, it is recognized that if the proper balance is found, each bubble in the foam forms an individual stable micelle.

In order for the present invention to be a commercial success, it was recognized that the proper combination of ingredients and processes which would allow the foam product to meet all of the following criteria was necessary. That is, the product had to be inexpensive; it must contain all inactive ingredients (except for the antibiotic) which do not react with the other components; it had to have pre-existing FDA approval of all components; it had to be stable at the clinical level; it had to have at least the same antimicrobial activity and be no more toxic than silver sulfadiazine cream ointments already on the market; it had to be painless in application; and, environmentally safe. Further, the bubble architecture had to have the water soluble portion on the outside, and the fat soluble portion of the compound on the inside; the product had to be resistant to desiccation and easily removable with water; and, finally the bubble size had to be correct.

The product as prepared by the following specific Examples meets all of these criteria.

EXAMPLE I

| Ingredient | % By Weight |
|---|---|
| 1. Silver Sulfadiazine | 1.00 |
| 2. White petrolatum | 8.22 |
| 3. Stearyl alcohol | 8.22 |
| 4. Isopropyl myristate | 3.28 |
| 5. Sorbitan monooleate | 0.55 |
| 6. Polyoxyl 40 stearate | 4.38 |
| 7. Propylene glycol | 3.83 |
| 8. Distilled Water | 60.22 |
| 9. Methylparaben | 0.30 |
| 10. Propane | 1.50 |
| 11. Isobutane | 8.50 |

An important feature of this invention is that the foam retains such a large proportion of water, at least 50% (by weight) of the product, but yet remains stable over long periods of time. With regard to remaining stable, the product will remain in a foam state for at least 24 hours after being applied. The product remains water soluble because of the large proportion of water therein.

The white petrolatum, stearyl alcohol, isopropyl myristate, sorbitan monooeate and polyoxyl 40 stearate are placed in a steel tank, heated to melt and agitated under heat of 75° C. until all ingredients are melted and thoroughly mixed to form the oil phase of the emulsion. The water and methylparaben are heated to 75° C. in a separate tank, with stirring, until all the methylparaben is dissolved to form the water phase of the emulsion. The water phase at 75° C. is added to the oil phase (at 65°-73° C.) with stirring continued until the resulting cream reaches 60°-65° C. Approximately five-sixths of the propylene glycol is placed in a tank and, while rapidly stirring, the silver sulfadiazine is added and stirring continued until all of the silver sulfadiazine is well suspended.

This suspension is added to the cream and the remaining propylene glycol used to wash out the mixing tank and added to the cream, with stirring continued until a uniform cream is obtained. The uniform cream is again heated to 75° C. and transferred to room temperature pressurized cans 10 at 35 pounds per square inch using the propane and isobutane as the propellant to form the foam product. The propellant serves to stabilize the individual bubble interior and hold all of the silver sulfadiazine molecule "tails" in place, along with the other foam components. The judicious amount of water holds the "heads" of the molecules together, and allows for the entire foam to become clinically water soluble.

EXAMPLE II

Foam compositions having the same formulation as EXAMPLE I except the aliphatic hydrocarbon propellant gas mixture employed is A-46 containing 50% propane and 50% isobutane to thereby employ 5.00%, by weight, propane and 5.00%, by weight, isobutane.

EXAMPLES III, IV, AND V

Foam compositions having the same formulation as EXAMPLE I except 1% of NEOSPORIN (a mixture of polymyxin B sulfate, bacitracin, zinc, and neomycin sulfate), 1% bacitracin, or 1% neomycin is substituted, respectively, for the 1% silver sulfadiazine.

EXAMPLES VI-XV

Foam compositions having the same formulation as EXAMPLES I, II, III, IV and V with the exception that 20% of ingredients 2-8 are replaced by 20% of xylocaine or benzocaine, but still maintaining at least 50% (by weight) water in the formulation.

It follows that the non-water ingredients can be varied within the following high and low ranges:

| INGREDIENTS COMPONENTS | EXAMPLE I (as listed above) | EXAMPLE I with water at 50% (as sugg. above) HIGH RANGE | EXAMPLES VI-XV with water at 60.22% (as sugg. above) LOW RANGE | POSSIBLE VARIABLE/FIXED AS PER EXAMPLES VI-XV |
|---|---|---|---|---|
| 1. Silver sulfadiazine | 1.00% | 1.00% | 1.00% | Fixed |
| 2. White petrolatum | 8.22% | 11.17% | 2.45% | Variable |
| 3. Stearyl alcohol (fatty alcl.) | 8.22% | 11.17% | 2.45% | Variable |
| 4. Isopropyl myristate (emollient) | 3.28% | 4.46% | 0.98% | Variable |
| 5. Sorbitan monooleate (emulsify.) | 0.55% | 0.75% | 0.16% | Variable |
| 6. Polyoxyl 40 stearate (emulsify.) | 4.38% | 5.95% | 1.30% | Variable |
| 7. Propylene glycol (humectant) | 3.83% | 5.20% | 1.14% | Variable |
| 8. Distilled Water | 60.22% | 50.00% | 60.22% | Variable |
| 9. Methylparaben (preservative) | 0.30% | 0.30% | 0.30% | Fixed |
| 10. Propane | 8.50% | 8.50% | 8.50% | Fixed |
| 11. Isobutane | 1.50% | 1.50% | 1.50% | Fixed |
| 12. Topical Anesthetic | 0.00% | 0.00% | 20.00% | Variable |
| TOTAL | 100.00% | 100.00% | 100.00% | |

These ranges follow by varying the water content in EXAMPLE I between 50% and 60.22% and varying the ingredients indicated in EXAMPLES VI-XV to be variable accordingly. EXAMPLES VI-XV suggest 20% of ingredients 2 to 7 of EXAMPLE I to be replaced by 20% of a topical anesthetic (Xylocaine or Benzocaine, both water soluble ingredients). It follows that an upper range of water is around 80.22%, which is the difference between 100% and the low-range sum of the other ingredients and is the total of the water and the water soluble anesthetic.

The foam product of this invention is applied from can 10 by a special dispenser nozzle 12 which can be fitted onto spout 14 of can 10. The special dispenser nozzle 12 has a thin, elongated opening 16 which applies a thin layer of foam over a wide area when valve 18 of can 10 is activated. The opening 16 is approximately three inches by one-eighth inch.

SUMMARY

From the foregoing specific EXAMPLES, it is readily seen that the present invention provides a successful and useful antibiotic. It is thought that this invention is the first known stable burn foam although there has been a long felt need for such a product. Further, the product of this invention is an inexpensive, painless, and easy applicable formulation that spreads faster and more evenly than possible by any cream formulation. In addition to eliminating any product waste, the foam of the present invention is clinically water soluble, and therefore washes off instantly without staining the skin. Further, it does not have the foul odor normally associated with silver sulfadiazine creams because the stable water-rich composition tends to contain these odors which generally come from the fat soluble portions of the silver sulfadiazine. The foam silver sulfadiazine formulation of the present invention requires no special handling, refrigeration or other precautions, and is equally efficacious, providing the same broad antimicrobial spectrum as, and no more toxicity than, the presently used silver sulfadiazine creams. Still further, the formulation is pH neutral and remains bioavailable and bactercidal for long periods of time. That is, the formulation does not deteriorate the effectiveness of the silver sulfadiazine.

In addition to the specific EXAMPLES set forth hereinabove, the present invention may be modified by the addition or substitution of other antibiotics; other analgesics; adding various enzymes such as collagenase, lipase, elastase, etc.; the addition of steroid preparations, such as hydrocortisone; the addition of vitamins A, E, B and others; the addition of growth and/or other hormones; the addition of biotin cofactors; the addition of other emollients, such as aloe, lanolin, and others; and, the addition of immunoglobulins, vaccines and other immumologic agents.

These and other modifications and variations of the present invention will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A pH neutral antibiotic formulation adapted for topical application as a clinically water soluble foam having a micelle structure and having the physical and chemical properties of remaining in the foam state for at least twenty-four (24) hours after application, comprising:

a quantity of approximately 1% by weight of an antibiotic having molecules of generally linear structure with one end thereof being more hydrophilic than the other, with the other end being more hydrophobic, suspended in an oil-in-water emulsion, said oil-in-water emulsion including between approximately 2.45 and 11.17% by weight of white petrolatum, between approximately 2.45 and 11.17% by weight of a fatty alcohol, between approximately 0.98 and 4.46% by weight of an emollient, between approximately 1.46 and 6.70% by weight of an emulsifying agent, between approximately 1.14 and 5.20% by weight of a humectant, a preservative and between 50% and up to 80.22% (by weight) water by weight; and, said emulsion being aerosolized by an inactive aliphatic hydrocarbon gaseous propellant of approximately 10% by weight into a stable micelle-like foam structure with membranes forming bubbles thereof including said antibiotic molecules of linear structure aligned with their more-hydrophilic ends generally facing away from a hollow chamber of the bubbles and the more-hydrophobic ends generally pointing down into the hollow chamber, whereby a more water soluble portion of the antibiotic is directed toward outside of the bubble and a more water insoluble portion is directed toward inside the bubble.

2. The antibiotic formulation of claim 1 wherein said oil-in-water emulsion includes an analgesic of between 0 and 20% by weight selected from the group of analgesics consisting of xylocaine and benzocaine.

3. The antibiotic formulation of claim 1 wherein said antibiotic is selected from the group of antibiotics consisting of bacitracin, neomycin, silver sulfadiazine and a mixture of polymyxin B sulfate, bacitracin, zinc, and neomycin sulfate.

4. The antibiotic formulation of claim 1 wherein said antibiotic formulation is adapted for treatment of skin abrasions and burned tissue and wherein said antibiotic is silver sulfadiazine.

5. The antibiotic formulation of claim 4 wherein the fatty alcohol is stearyl alcohol, the emollient is isopropyl myristate, the emulsifying agent is a quantity of sorbitan monooleate and a quantity of polyoxyl 40 stearate, the humectant is propylene glycol, and the preservative is methylparaben and the inactive aliphatic hydrocarbon gaseous propellant is a mixture of propane and isobutane.

6. The antibiotic formulation of claim 4 wherein the inactive aliphatic hydrocarbon gaseous propellant is a mixture of 85% isobutane and 15% propane.

7. The antibiotic formulation of claim 4 wherein said oil-in-water emulsion includes, by weight, approximately 8.22% white petrolatum, 8.22% stearyl alcohol, 3.28% isopropyl myristate, 0.55% sorbitan monooleate, 4.38% polyoxyl 40 stearate, 3.83% propylene glycol, 60.22% water, and 0.30% methylparaben and the inactive aliphatic hydrocarbon gaseous propellant includes, by weight, 5.00% propane and 5.00% isobutane.

8. The antibiotic formulation of claim 4 wherein said oil-in-water emulsion includes, by weight, approximately 8.22% white petrolatum, 8.22% stearyl alcohol, 3.28% isopropyl myristate, 0.55% sorbitan monooleate, 4.38% polyoxyl 40 stearate, 3.83% propylene glycol, 60.22% water, and 0.30% methylparaben and the inactive aliphatic hydrocarbon gaseous propellant includes, by weight, 1.50% propane and 8.50% isobutane.

9. A method of making a pH neutral antibiotic formulation that is dispensable as a stable water soluble foam to permit painless application and removal thereof and capable of remaining in the foam state for a period of at least twenty-four (24) hours after dispensing, comprising the steps of:

combining approximately 1% by weight of an antibiotic with between approximately 2.45 and 11.17% by weight of white petrolatum, between approximately 2.45 and 11.17% by weight of a stearyl alcohol, between approximately 0.98 and 4.46% by weight of isopropyl myristate, between approximately 0.016 and 0.75% by weight of sorbitan monooleate, between approximately 1.30 and 5.95% by weight of polyoxyl 40 stearate, between 1.14 and 5.20% by weight of propylene glycol, methylparaben and between 50% and up to 80.22% (by weight) water by weight;

heating this mixture with stirring to approximately 75° C.;

maintaining this temperature and stirring until all ingredients are in the liquid state and an oil-in-water emulsion is obtained, and while hot enough to maintain the liquid state placing the liquid into aerosol cans and pressurizing the cans to approximately thirty-five pounds per square inch pressure using an inactive aliphatic hydrocarbon gaseous propellant.

10. The method of claim 9 wherein the antibiotic is silver sulfadiazine and the quantities of all ingredients employed, by weight, are approximately:

1.00% silver sulfadiazine, 8.22% white petrolatum, 8.22% stearyl alcohol, 3.28% isopropyl myristate, 0.55% sorbitan monocleate, 4.38% polyoxyl 40 stearate, 3.83% propylene glycol, 60.22% distilled water, 0.30% methylparaben and, 10.00% inactive aliphatic hydrocarbon gaseous propellant.

11. The method of claim 10 wherein the 10.00%, by weight, inactive aliphatic hydrocarbon gaseous propellant is a mixture of 15%, by weight, propane and 85%, by weight, isobutane.

12. The method of claim 10 wherein the 10.00% by weight, of inactive aliphatic hydrocarbon gaseous propellant comprises 50%, by weight propane and 50%, by weight isobutane.

* * * * *